United States Patent [19]

Leclerc

[11] Patent Number: 4,525,166

[45] Date of Patent: Jun. 25, 1985

[54] ROLLED FLEXIBLE MEDICAL SUCTION DRAINAGE DEVICE

[75] Inventor: Roland-Yves J. Leclerc, Nogent-le-Rotrou, France

[73] Assignee: Intermedicat GmbH, Emmenbrucke, Switzerland

[21] Appl. No.: 442,583

[22] Filed: Nov. 18, 1982

[30] Foreign Application Priority Data

Nov. 21, 1981 [DE] Fed. Rep. of Germany ....... 3146266

[51] Int. Cl.³ ............................................ A61M 37/00
[52] U.S. Cl. ...................................... 604/133; 604/30; 604/313
[58] Field of Search .......... 604/30, 133, 134, 313–318, 604/320, 322, 323, 326; 128/760, 767; 141/10, 65, 114; 417/89, 90

[56] References Cited

U.S. PATENT DOCUMENTS

| | | | |
|---|---|---|---|
| 3,233,609 | 2/1966 | Leucci | 604/30 |
| 3,572,340 | 3/1971 | Lloyd et al. | 604/133 |
| 3,832,999 | 9/1974 | Crilly | 604/323 |
| 3,871,377 | 3/1975 | Treace | 604/133 |
| 4,112,947 | 9/1978 | Nehring | 604/133 |
| 4,187,860 | 2/1980 | Villari | 128/776 |
| 4,319,573 | 3/1982 | Whitlock | 604/323 |
| 4,386,930 | 6/1983 | Cianci | 604/307 |

OTHER PUBLICATIONS

Mechanical Engineers' Handbook, Baumeister et al, Editor, McGraw-Hill Book Company, Inc., New York, 1958, pp. 5-15 to 5-17.

*Primary Examiner*—C. Fred Rosenbaum
*Assistant Examiner*—J. L. Kruter
*Attorney, Agent, or Firm*—Kenyon & Kenyon

[57] ABSTRACT

A suction drainage device is disclosed which comprises a receptacle communicated with a body cavity via an inlet tube. The receptacle is formed as a bellows, flat receptacle, foil or sheet bag, or foil or sheet tube and the like which can be folded or rolled up. A flexible check valve in the form of a foil or sheet valve, or flutter valve, is disposed inside the receptacle. The inlet tube is provided on a side of one edge of the receptacle so that the receptacle can be rolled up over a long roll path without interference from the valve. The device can be manufactured at low cost.

18 Claims, 7 Drawing Figures

ROLLED FLEXIBLE MEDICAL SUCTION DRAINAGE DEVICE

BACKGROUND OF THE INVENTION

The present invention relates to a suction drainage device, particularly a medical suction drainage device adapted to be communicated with a body cavity to drain body fluids therefrom. More particularly, the present invention relates to a medical suction drainage device which can be used as a receptacle for body fluids, e.g. wound secretions and/or excretions, and in which a vacuum can be created by manually conditioning the device.

In the postoperative draining of wounds and the like, it is common practice to insert a catheter, for example a flexible drainage catheter, into the wound, which is closed for example by sutures or surgical clamps, to remove fluids which form as the wound heals. After the wound heals, the catheter is removed by extraction. It has been found to be advantageous to apply a vacuum to such flexible drainage catheters which frequently have multiple perforations over a part of their length. The vacuum not only speeds up the removal of fluids from the wound but also presses the cut edges of the surgical wound together, thereby stimulating rapid tissue granulation and healing of the wound. Systems which include a flexible catheter drainage tube with multiple perforations in the wall of the catheter and a pre-evacuated vacuum reservoir connected to the catheter are known, for example, as Redon drainage systems.

Such drainage systems can be supplied as reusable devices and as single use disposable devices. Single use disposable systems are advantageous for hygienic and economic reasons and, as a vacuum source, utilize, for example, a glass bottle evacuated to a predetermined partial vacuum of 0.1 bar, for example. The vacuum existing in such systems is in many cases qualitatively indicated on a dial. Although reusable systems can be worn by ambulatory patients, they are not entirely satisfactory because of susceptibility to breaking, their weight, the unfavorable geometric shape of the glass bottle, and especially because the wall thickness of the tube required for stability under high vacuum results in a clumsy and relatively rigid drainage system.

Devices intended for a single disposable use, normally made of plastics, are often more favorable in the above respects because they are at least lightweight and unbreakable. Such single use systems can comprise, for example, a flexible plastic container which can be compressed like an accordion and expanded by a spring force. A vacuum chamber is created in the container by compression, for example, and after the drainage catheter has been connected to the container, the necessary suction is created by expansion aids in the container.

While on the one hand it is desirable to have a relatively high vacuum available from the vacuum source to promote healing, a high vacuum is disadvantageous on the other hand because the tissue adjacent to the wound on the outside of the catheter can be sucked and pressed into the holes of the catheter under high vacuum, particularly in the case of brain and breast operations, so that upon the removal, i.e. extraction of the catheter, the wound can be torn open again and new trauma can be created in the original wound. Another disadvantage results from the presence of the collected body fluids in the receptacle as unrestrained liquids since such fluids, which can be infected, can through inadvertence of medical personnel flow back into the catheter. In addition, if a glass bottle is used and breaks, the fluids escaping from the broken bottle can contaminate the environment and medical personnel.

The above defects are largely remedied by the device described in U.S. Pat. No. 3,572,340 (Lloyd et al.) which comprises a collapsible bag receptacle of flexible material filled with a material which absorbs body fluids as the volume of the material expands. In the center of each of two opposite edges of the receptacle bag an opening is formed provided with a connector or nipple. The opening and nipple in one edge form an inlet for body fluids and the opening and nipple in the other edge form an outlet for air. The body fluid inlet nipple has a ball valve associated with it to prevent the return flow of body fluids from the receptacle bag into the patient. A disadvantage in using a ball valve is clogging of the ball valve particularly when the body fluids being sucked out of a wound include a colloid-containing protein solution which agglutinates, especially at the body temperatures at which the bags are being worn where coagulation of the solution readily occurs. Since the bag receptacle can not be rolled up over a large roll length because of the two centrally arranged nipples, the bag receptacle cannot be fully deaerated and the full volume expansion capacity of the filling material is not utilized for the absorption of body fluids. Hence, the bag receptacle must be changed more frequently. When the bag receptacle is made with only the inlet nipple, problems arise with deaeration because the ball valve must be deactivated to allow the air to escape. To alleviate those problems, the ball valve can be lodged in a separate part which is coupled through fittings with the inlet nipple only after evacuation occurs. This additional part unduly increases the cost of the device intended for a single disposable use. Another factor contributing to cost is the design of the valve as a ball valve.

OBJECTS AND SUMMARY OF THE INVENTION

It is an object of the present invention to provide an inexpensive, single use disposable device suitable for draining body fluids particularly from wounds. It is another object to provide such a device which is easy and quick to handle and in which the vacuum, required for maximum utilization of the suction effect of a fluid-sorbing material disposed in the device, is manually created.

The above and other objects are achieved according to the invention by providing a suction drainage device comprising a flexible receptacle in which is disposed a sorbent material, and a flexible check valve which permits the receptacle to be rolled-up over a relatively long roll path, so that good deaeration and maximum utilization of the suction effect of the sorbent material are achieved.

The flexible valve of the invention opens and closes in response to the condition of the flexible receptacle and has the advantages that it does not clog up in the presence of a coagulating solution and allows the receptacle to be rolled or folded over a long roll path.

The receptacle is substantially collapsible so that it can be substantially evacuated of gases, i.e. air. Further in accordance with the invention, the receptacle is a bag-type receptacle, made for example from a heat-sealed transparent plastic film, which among other things is impervious to odor and to bacteria, and is filled with the sorbent material, preferably an absorbent material such as an open-pore, highly fluid-absorbing spongy material which is capable of absorbing body fluids, particularly wound fluids, and expanding as it absorbs fluids to erect and expand the compressed receptacle by its inherent elasticity and create a suction effect. Substances which increase in volume as they sorb fluids and create the above effects are also suitable as filling materials for the receptacle. Sorbent materials in the interior of the receptacle support by capillary or sorption-type physical activity drainage of body fluids from a wound, for example, in the presence, at least initially, of a vacuum.

Open-pore filling material of a spongy structure include, for example, polyurethane foams of suitable resilience. An absorbent material which increases in volume as it absorbs liquid is available under the designation "Favor" from Chemische Fabrik Stockhausen GmbH. of Krefeld, West Germany. Combinations of an open pore filling material and a sorbent material which increase in volume as they sorb liquid can also be used. The open pore filling material and the sorbent material may sorb liquid by molecular cohesion. One or more bactericidal agents can be incorporated in the material so as to prevent bacterial growth in the event of infection and the formation of any gas that the bacterial growth would cause.

According to the invention, the filling material can comprise laminaria (kelp) which swells as it sorbs liquid and has liquid retaining properties so as to enhance retention of sorbed liquids and substantially prevent a return flow of liquid from the receptacle.

A tube secured as by welding between the two receptacle-forming sheets or foils is provided as an inlet to the interior of the receptacle and forms, when completely filled, in cooperation with sorbing by the sorbent material, a liquid column required for capillary action.

Because small volumes are involved, low Shore hardness tubes are advantageously used for the drainage line from the wound to the device, resulting in greater flexibility in applying the device and in a more secure retention of the drainage line in the area of the wound. The liquid column required to initiate the capillary action can be formed by a small, temporary vacuum created, for example, by rolling or folding the evacuated closed receptacle, which can bring the liquid up to the sorbing medium. The tube may have at its end a customary projection or fitting which mates with a screw or plug connection comprising a male and female conical projection or fitting, thereby forming a detachable connection used, for example, when replacing the receptacle.

Still further according to the invention, a shut-off device is provided to interrupt the drainage-promoting suction effect or to control access to the interior of the bag receptacle. According to one embodiment, the shut-off device is a sliding clamp which embraces the inlet tube and continuously narrows the tube lumen upon displacement of the clamp through an acute-angle recess. According to another embodiment, the shut-off device is a needle valve comprising a housing and a valve spindle inserted in the inlet tube.

An additional tube whose length can be fixed as needed may be provided to extend from the detachable connection to the drainage catheter positioned in the wound. The additional tube terminates in a tube projection or fitting which can be attached to the drainage catheter.

Fastening eyelets provided at the top of the receptacle bag permit the receptacle bag to be attached by suitable suspension or fastening means on the ambulatory patient himself or on an external apparatus. Depending on the location of the wound, the receptacle can be contoured to follow the anatomy and sized corresponding to the amount of body fluid expected.

The vacuum or suction effect required for proper drainage is created by and within the receptacle according to the invention in a simple manner. The volume of air contained within the receptacle is removed for example by folding the receptacle or rolling it up. The compressed receptacle is then temporarily closed with the shut-off device. The total drainage path to the catheter is thereafter connected, after which the shut-off device is opened. The vacuum as well as the capillary action or the sorption properties of the filling material contained in the receptacle then respectively bring about, as the receptacle expands, a gentle removal of body fluids and their collection in the receptacle itself. If desired, the vacuum can be created by evacuating with an external vacuum source.

The inlet tube with the flexible valve may be located in the center or on the side of one edge of the receptacle. Accordingly, the bag-type receptacle can be rolled up for deaeration starting from the edge opposite to the inlet tube edge and progressing crosswise to the inlet tube, or from an edge parallel to the inlet tube and progressing parallel to the inlet tube, so that the roll path for the receptacle is always long. The flexible, or sheet or foil valve is inexpensive, and it is located within the receptacle together with the inlet tube to which it is fastened. Therefore, it is only necessary to heat-seal the receptacle edge through which the inlet tube protrudes. For deaeration of the receptacle, the flexible valve is made inoperative by inserting a thin tube through the inlet tube and through the flexible valve into the receptacle. As the receptacle is being rolled up, air escapes through the thin tube, and as soon as the latter has been pulled out, the flexible valve closes and is operative to prevent air from entering into the receptacle and a return flow of fluids from the receptacle.

The flexible valve ensures hygienic and reliable operation of the device.

The above and other objects, features, aspects and advantages of the invention will be more apparent from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like numerals indicate similar parts and in which.

DESCRIPTION OF THE PREFERRED EMBODIMENTS

Figure 1:
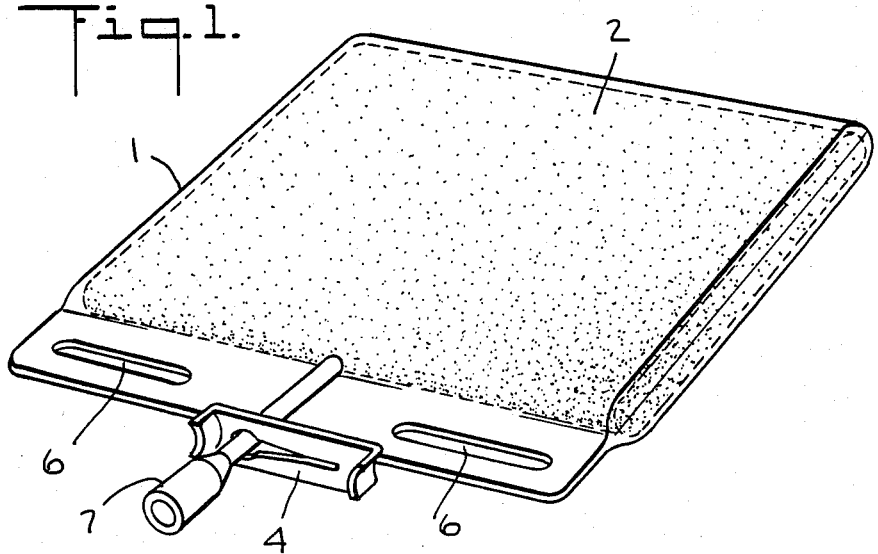
FIG. 1 is a perspective view of one embodiment of a suction drainage device according to the invention with its inlet open and the bag receptacle fully expanded.
Figure 2:
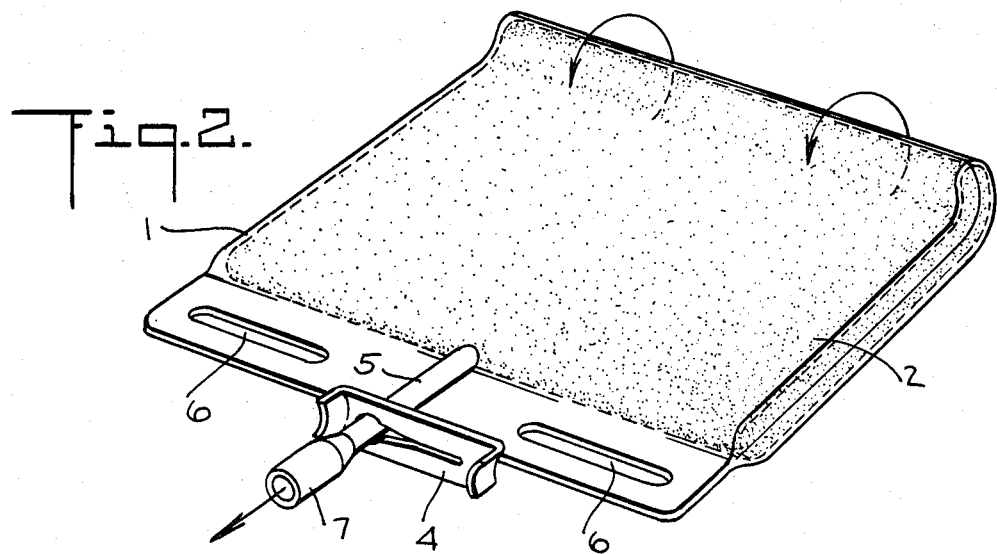
FIG. 2 is a perspective view of the device of FIG. 1 as rolling of the bag receptacle is started to start evacuation of air from the receptacle.
Figure 3:
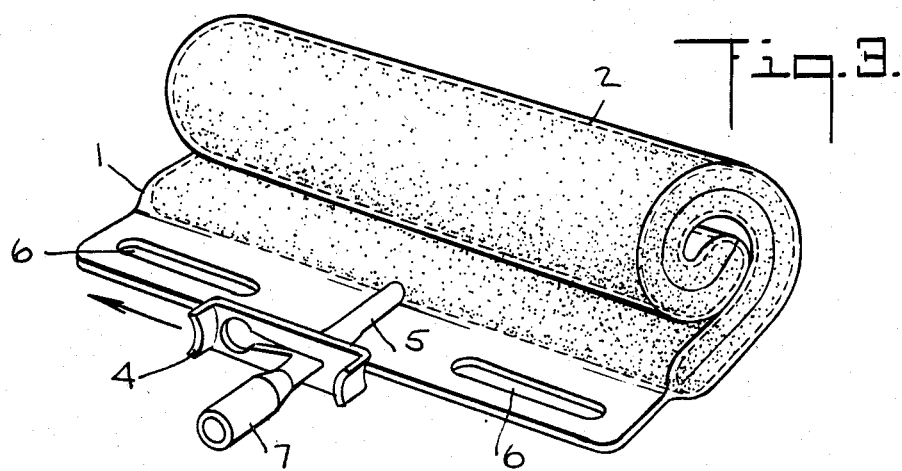
FIG. 3 is a perspective view of the device of FIG. 1 with the bag receptacle fully rolled and the inlet closed.

Referring first to FIGS. 1-3, a drainage device comprises a receptacle 1 in the form of a flat, flexible foil or sheet bag, or tube, or a bellows, the cavity of which is completely filled with a sorbent material 2 in the form of a thick strip of material. The receptacle 1 is sealed around its perimeter and has at one edge two fastening eyelets 6 by means of which the receptacle can be suspended on the patient or on a holding device.

The receptacle can be made of a polymeric mono- or laminate film which is substantially impervious to gas, or a metallized polymeric mono- or laminate film, which is also substantially impervious to gas. Preferably, the material of which the receptacle is made can be sterilized.

In the center of one edge of the receptacle is disposed an inlet tube 5 opening into the interior of the receptacle. The tube carries a socket 7 of a plug coupling for connecting the tube to a catheter which is inserted in a body cavity. The inlet tube 5 is heat-sealed into a receptacle edge and can be closed and opened by means of a sliding clamp 4 of the continuous action type having an acute angle or narrowing recess. No other outlet or inlet openings are provided on the receptacle 1.

By rolling up the receptacle 1 (FIGS. 2 and 3) air is forced out of the receptacle through the open tube 5. After the receptacle has been rolled, the tube 5 is closed with the sliding clamp 4 to close the receptacle and opened again only after the tube has been connected to the catheter. The vacuum and capillary action of the filling material 2 remove body fluids from the wound and transfer the fluids into receptacle 1 as the latter expands.

As material 2 there may be used, instead of a suitable foam, laminaria (kelp) in granular form or incorporated in foam molded parts. Laminaria swells by absorption of liquid and does not later release the liquid. This is advantageous because a return flow of the fluid collected in receptacle 1 into the wound or body cavity is prevented without a check valve. The suction effect of this material is considerable, and there is no need for a further vacuum as a suction aid.

Figure 4:
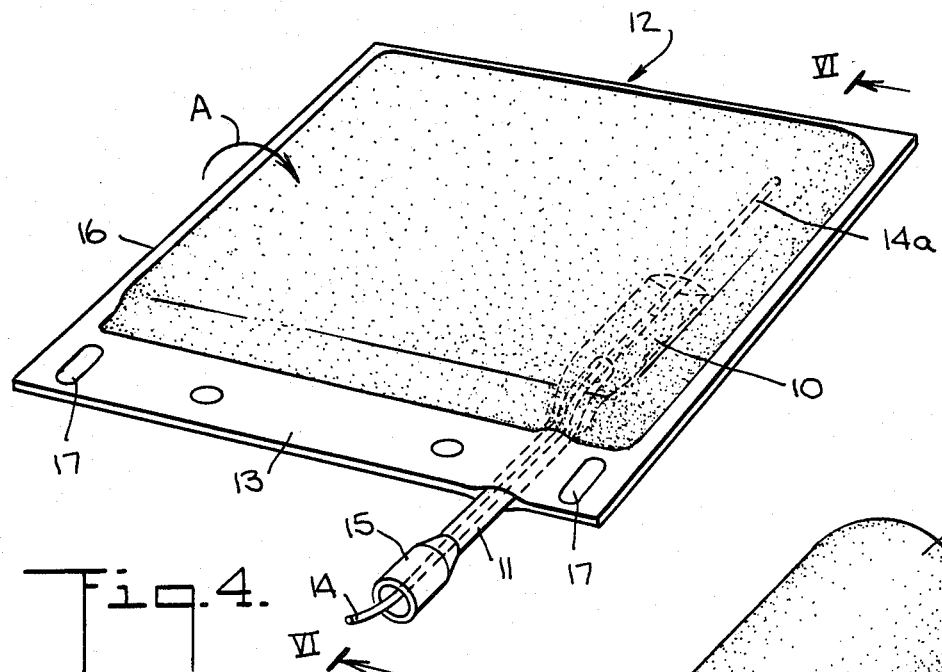
FIG. 4 is a perspective view of another embodiment of a device according to the invention with the inlet and the flexible check valve open, and the bag receptacle fully expanded.
Figure 5:
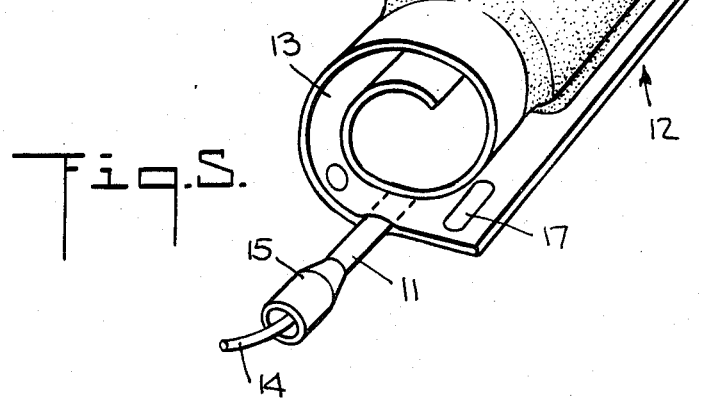
FIG. 5 is a perspective view of the device of FIG. 4 with the bag receptacle fully rolled.
Figure 6:
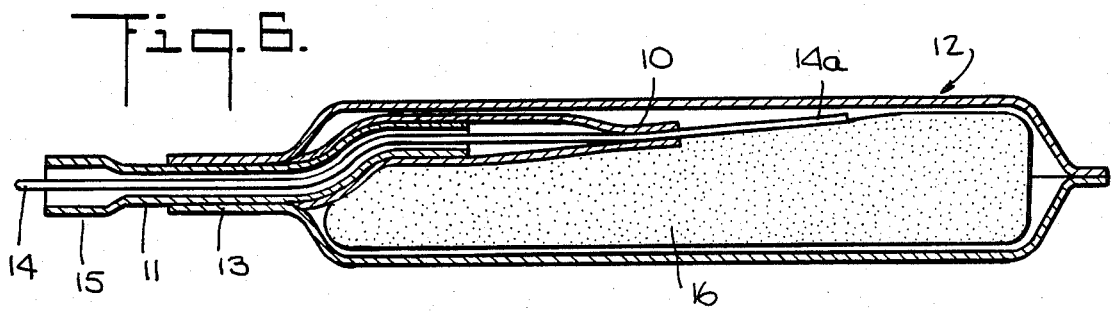
FIG. 6 is a section view taken along line VI—VI in FIG. 4.
Figure 7:
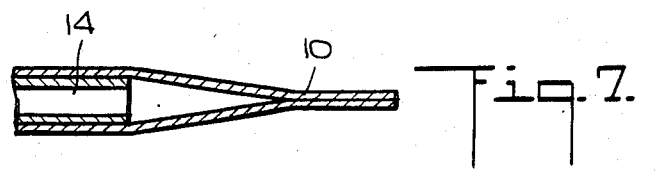
FIG. 7 is a longitudinal section view of the closed check valve of the device of FIG. 4.

In the embodiment according to FIG. 4, an inlet tube 11 opening into a receptacle 12 made of foil or sheet material is disposed adjacent a side of the edge 13 of the receptacle and is welded to the edge 13. Holes 17 are provided in edge 13 for attaching the receptacle 12 to the body of the patient. At the outer end of the inlet tube 11, a socket 15 of a plug coupling is provided for connection to a drainage tube, while at the inner end of the inlet tube 11, a flexible foil or sheet or flutter valve 10 is provided. The flutter valve 10 comprises two superposed, flexible foils or sheets which are joined together along their longitudinal edges and are left open at the end disposed in the receptacle. Since it is not practical to roll the receptacle 12 of the embodiment of FIG. 4 as illustrated and described with respect to FIGS. 1-3 because of a shortened roll path, receptacle 12 is rolled up in the direction of arrow A parallel to the axis of the inlet tube 11.

In order to by-pass the flutter valve 10, a thin tube 14 is inserted through socket 15, inlet tube 11 and flutter valve 10, with the inner end 14a of the tube 14 protruding out of the flutter valve 10 into receptacle 12, thereby permitting air to leave the receptacle 12 as it is rolled. After the receptacle 12 has been sufficiently deaerated, the thin tube 14 is pulled out and the flutter valve 10 closes. The vacuum in receptacle 12 can be then utilized for sucking fluid from a body cavity into sorbent material 16 inside receptacle 12. The suction effect of the vacuum is aided by the capillary action of the fluid-sorbing material 16.

The advantages of the present invention, as well as certain changes and modifications of the disclosed embodiments thereof, will be readily apparent to those skilled in the art. It is the applicant's intention to cover by his claims all those changes and modifications which could be made to the embodiments of the invention herein chosen for the purpose of disclosure without departing from the spirit and scope of the invention.

What is claimed is:

1. A suction drainage device comprising a receptacle of flexible material capable of being folded, rolled and the like, fluid-sorbing material disposed in the receptacle, fluid passage means coupling the exterior of the receptacle to the interior of the receptacle and adapted to be communicated with a source of fluid located at the exterior of the receptacle, and a flexible check valve disposed in the receptacle at a side of one edge of the same and being operative to seal and open communication between the interior of the receptacle and said passage means in response to the condition of the receptacle and a thin tube extending through the flexible valve to the exterior of the receptacle through said passage means which is adapted to be pulled out of the valve and said passage means.

2. A device according to claim 1 wherein the fluid-sorbing material is a resilient, compressible open-pore material.

3. A device according to claim 2 wherein the fluid-sorbing material comprises laminaria disposed in the open-pore material.

4. A device according to claim 1 wherein the fluid-sorbing material is an open-pore material which becomes soft and flexible and expands in volume upon sorbing fluid.

5. A device according to claim 1 wherein the fluid-sorbing material is a material which sorbs fluid by molecular cohesion and expands in volume as fluid is sorbed.

6. A device according to claim 1 wherein the fluid-sorbing material comprises an open-pore material which becomes soft and flexible and expands in volume upon sorbing fluid, and a material which sorbs fluid by molecular cohesion.

7. A device according to claim 1 wherein the fluid-sorbing material comprises at least one bactericidal agent.

8. A device according to claim 1 wherein the fluid-sorbing material comprises laminaria.

9. A device according to claim 1 wherein the receptacle material comprises a polymeric mono- or laminate film.

10. A device according to claim 1 wherein the receptacle material comprises a metallized polymeric mono- or laminate film.

11. A device according to claim 1 wherein the device comprises materials which can be sterilized.

12. A device according to claim 1 wherein said passage means comprises an inlet tube.

13. A device according to claim 12 wherein said inlet tube is made of a material of low Shore hardness.

14. A device according to claim 12 and including a shutoff device for selectively closing and opening the inlet tube.

15. A device according to claim 12 wherein the receptacle is rectangular and the inlet tube is located on one long side of the receptacle.

16. A device according to claim 1 wherein the flexible check valve comprises superposed flexible sheets sealed along their longitudinal edges and open at their ends, the superposed sheets being sealingly connected to the inlet tube.

17. A suction drainage device according to claim 1 further including a clamp embracing the passage means operative to selectively open and close the passage means.

18. A suction drainage device according to claim 1 and comprising a thin tube extending through the flexible valve to the exterior of the receptacle through said passage means which is adapted to be pulled out of the valve and said passage means.

* * * * *